(12) United States Patent
Sahouani

(10) Patent No.: US 7,247,723 B2
(45) Date of Patent: Jul. 24, 2007

(54) METALLIC CHROMONIC COMPOUNDS

(75) Inventor: Hassan Sahouani, Hastings, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/996,834

(22) Filed: Nov. 24, 2004

(65) Prior Publication Data

US 2006/0110922 A1    May 25, 2006

(51) Int. Cl.
  C07D 251/48   (2006.01)
  C01G 5/00     (2006.01)
  C01G 7/00     (2006.01)
  C01G 55/00    (2006.01)

(52) U.S. Cl. ...................... 544/198; 977/828
(58) Field of Classification Search ............... 544/198; 977/828

See application file for complete search history.

(56) References Cited

U.S. PATENT DOCUMENTS

| | | | |
|---|---|---|---|
| 5,948,487 A | 9/1999 | Sahouani et al. | |
| 6,051,290 A | 4/2000 | Sahouani et al. | |
| 6,395,354 B1 | 5/2002 | Sahouani et al. | |
| 6,488,866 B1 | 12/2002 | Sahouani et al. | |
| 6,538,714 B1 | 3/2003 | Sahouani et al. | |
| 6,574,044 B1 | 6/2003 | Sahouani et al. | |
| 6,645,578 B2 | 11/2003 | Sahouani et al. | |
| 6,699,533 B2 | 3/2004 | Sahouani et al. | |
| 2002/0066885 A1 | 6/2002 | Sahouani et al. | |
| 2002/0132065 A1 | 9/2002 | Sahouani et al. | |

FOREIGN PATENT DOCUMENTS

| | | |
|---|---|---|
| WO | WO 98/37997 A2 | 9/1998 |
| WO | WO 00/22463 A1 | 4/2000 |
| WO | WO 2005/012488 A2 | 2/2005 |

OTHER PUBLICATIONS

Barbic et al., "Single Crystal Silver Nanowires Prepared by the Metal Amplification Method", Journal of Applied Physics, (Jun. 1, 2002), pp. 9341-9345, vol. 91, No. 11, 2002 American Institute of Physics.
Kawasaki et al., "Controlled Layering of Two-Dimensional J-Aggregate of Anionic Cyanine Dye on Self-Assembled Cysteamine Monolayer on Au(111)", Langmuir, (2000), pp. 5409-5417, vol. 16, No. 12, 2000 American Chemical Society.
Pardavi-Horvath et al., "Iron-Alumina Nanocomposites Prepared by Ball Milling", IEEE Transactions on Magnetics, (Sep. 1992), pp. 3186-3188, vol. 28, No. 5.
Lydon, "Chromonic Mesophases", Current Opinion in Colloid and Interface Science, (2004), pp. 480-490, vol. 8.
Ding et al., "Structure Analysis of Nanowires and Nanobelts by Transmission Electron Microscopy", J. Phys. Chem. B, (2004), pp. 12280-12291, vol. 108, No. 33.
Attwood et al., "Lyotropic Mesophase Formation by Anti-Asthmatic Drugs", Mol. Cryst. Liq. Cryst., (1984), pp. 349-357, vol. 108, Gordon and Breach, Science Publishers, Inc.
Brinker et al., "Review of Sol-Gel Thin Film Formation", Journal of Non-Crystalline Solids, (1992), pp. 424-436, vol. 147&148, Elsevier Science Publishers B. V.
Lydon, "Chapter XVIII, Chromonics", Handbook of Liquid Crystals, (1998), pp. 981-1007, vol. 2 B: Low Molecular Weight Liquid Crystals II, Wiley-VCH Verlag GmbH. D-60469 Weinheim.
Aguirre et al., "CTAB Mediated Reshaping of Metallodielectric Nanoparticles", Nano Letters, (2003), pp. 1707-1711, vol. 3, No. 12, American Chemical Society.
Medintz et al., "Self-Assembled Nanoscale Biosensors Based on Quantum Dot FRET Donors", Nature Materials, (Sep. 2003), pp. 630-638, vol. 2, Nature Publishing Group.
Kumar et al., "Linear Superclusters of Colloidal Gold Particles by Electrostatic Assembly on DNA Templates", Advanced Materials, (Mar. 2, 2001), pp. 341-344, vol. 13, No. 5, Wiley-VCH Verlag GmbH, D-69469 Weinheim.
Hong et al., "Ultrathin Single-Crystalline Silver Nanowire Arrays Formed in an Ambient Solution Phase", Science, (Oct. 12, 2001), pp. 348-351, vol. 294.

(Continued)

Primary Examiner—Venkataraman Balasubramanian
(74) Attorney, Agent, or Firm—Lisa P. Fulton

(57) ABSTRACT

A chromonic compound represented by one of the following general structures:

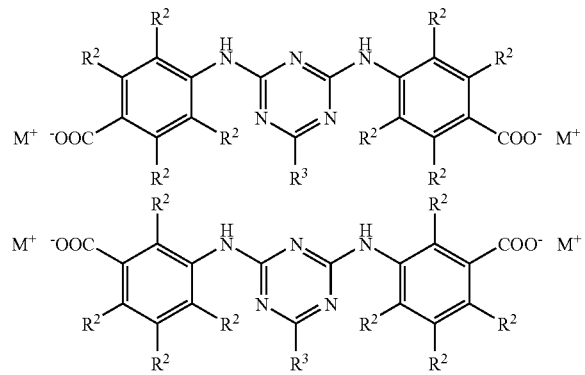

wherein each $R^2$ is independently selected from the group consisting of electron donating groups, electron withdrawing groups, and electron neutral groups, $R^3$ is selected from the group consisting of substituted and unsubstituted heteroaromatic rings and substituted and unsubstituted heterocyclic rings, said rings being linked to the triazine group through a nitrogen atom within the ring of $R^3$, and M+ is a noble or transition metal cation.

19 Claims, 1 Drawing Sheet

OTHER PUBLICATIONS

Zhang et al., "Polymer Microgels: Reactors for Semiconductor, Metal and Magnetic Nanoparticles", JACS, (2004), 7908-7914, vol. 126, No. 25, American Chemical Society.

Huang et al., "Nanowire Arrays Electrodeposited from Liquid Crystalline Phases", Advanced Materials, (Jan. 4, 2002), pp. 61-64, vol. 14, No. 1, Wiley-VCH Verlag GmbH, D-69469 Weinheim.

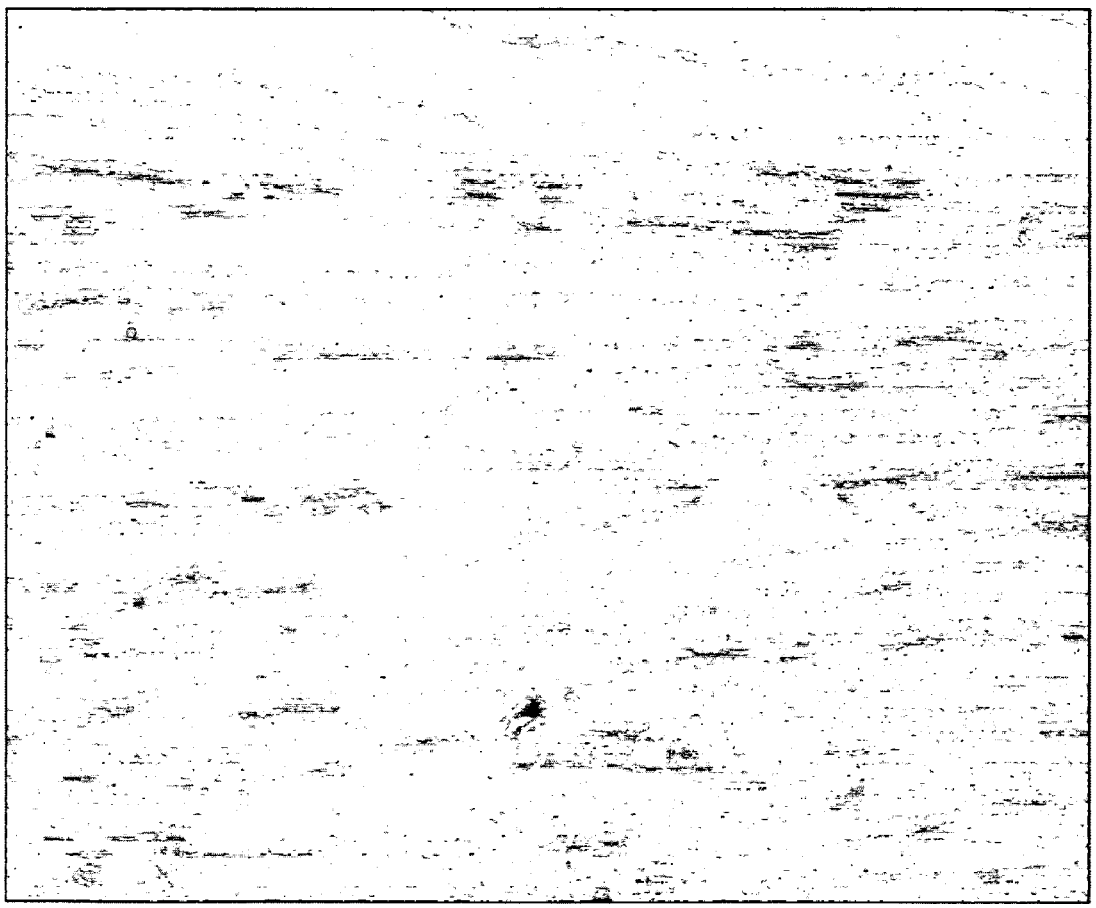

METALLIC CHROMONIC COMPOUNDS

FIELD

This invention relates to chromonic compounds, and in another aspect, to methods for making metallic nanostructures using the chromonic compounds.

BACKGROUND

In recent years, there has been increasing research effort to develop metal structures in the nanoscale range (that is, in the 0.1 to 100 nm range) for a variety of technological applications such as, for example, electronic and optical devices, labeling of biological material, magnetic recording media, and quantum computing.

Numerous approaches have been developed for synthesizing/fabricating metal nanostructures such as, for example, metal nanowires, nanorods, nanotubes, and nanoribbons. Current approaches include, for example, fabricating metal nanowires by the electroless deposition of metal into the pores of nanoporous membranes by a metal amplification process (see, for example, Barbic et al., J. Appl. Phys., 91, 9341 (2002)) and fabricating metal nanowires/nanotubes by a vapor-liquid-solid (VLS) process in which involves the dissolution of gaseous reactants in nanosized liquid droplets of the metal solvent, followed by nucleation and growth of single crystalline wires (see, for example, Ding et al., J. Phys. Chem. B 108, 12280 (2004)). A challenge that remains, however, is controlling the size and shape of metallic nanostructures, as well as their orientation and distribution, particularly on a large scale.

SUMMARY

In view of the foregoing, it has been recognized that there is a need for a method for making nanostructures that provides control over the size and shape of metallic nanostructures, as well as their orientation and distribution, over a relatively large area.

Briefly, in one aspect, the present invention provides a chromonic compound that is useful in methods for making metallic nanostructures. The compound can be represented by one of the following general structures:

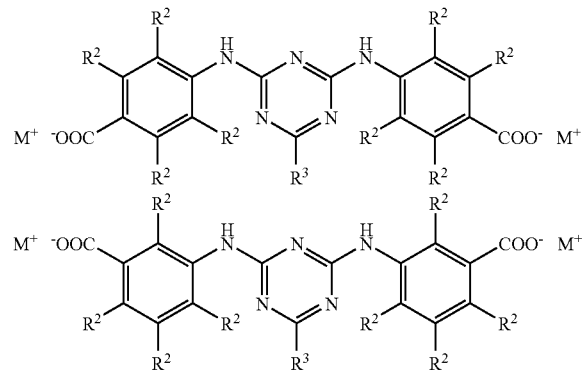

wherein
each $R^2$ is independently selected from the group consisting of electron donating groups, electron withdrawing groups, and electron neutral groups, $R^3$ is selected from the group consisting of substituted and unsubstituted heteroaromatic rings and substituted and unsubstituted heterocyclic rings, said rings being linked to the triazine group through a nitrogen atom within the ring of $R^3$, and a counterion being present if $R^3$ is a substituted or unsubstituted heteroaromatic ring, and $M^+$ is a noble or transition metal cation.

As used herein, "chromonic compounds" refers to large, multi-ring molecules typically characterized by the presence of a hydrophobic core surrounded by various hydrophilic groups (see, for example, Attwood, T. K., and Lydon, J. E., Molec. Crystals Liq. Crystals, 108, 349 (1984)). The hydrophobic core can contain aromatic and/or non-aromatic rings. When in solution, these chromonic materials tend to aggregate into a nematic ordering characterized by a long-range order.

In another aspect, the present invention provides a method of making oriented nanostructures using the compound of the invention. The method comprises applying a solution comprising the compound of the invention to the surface of a substrate, and reducing the metal.

DESCRIPTION OF DRAWINGS

The FIGURE is an optical micrograph showing silver nanowires.

DETAILED DESCRIPTION

The compound of the invention can be represented by one of the following general structures:

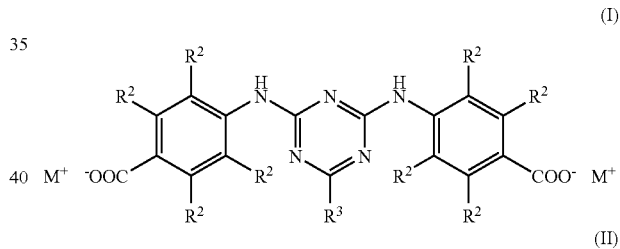

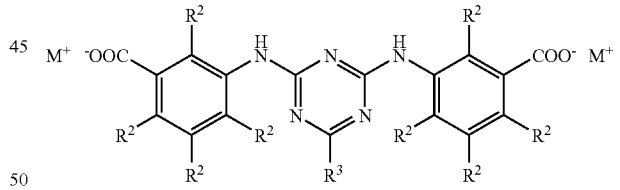

wherein
each $R^2$ is independently selected from the group consisting of electron donating groups, electron withdrawing groups, and electron neutral groups, $R^3$ is selected from the group consisting of substituted and unsubstituted heteroaromatic rings and substituted and unsubstituted heterocyclic rings, said rings being linked to the triazine group through a nitrogen atom within the ring of $R^3$, and a counterion being present if $R^3$ is a substituted or unsubstituted heteroaromatic ring, and $M^+$ is a noble or transition metal cation.

The general structures above show orientations in which the carboxy group is para with respect to the amino linkage to the triazine backbone of the compound (formula I) and in which the carboxy group is meta with respect to the amino linkage to the triazine backbone (formula II). The carboxy group can also be a combination of para and meta orientations (not shown). Preferably, the orientation is para.

Preferably, each $R^2$ is hydrogen or a substituted or unsubstituted alkyl group. More preferably, $R^2$ is independently selected from the group consisting of hydrogen, unsubstituted alkyl groups, alkyl groups substituted with a hydroxy or halide functional group, and alkyl groups comprising an ether, ester, or sulfonyl. Most preferably, $R^2$ is hydrogen.

$R^3$ can be, but is not limited to, heteroaromatic rings derived from pyridine, pyridazine, pyrimidine, pyrazine, imidazole, oxazole, isoxazole thiazole, oxadiazole, thiadiazole, pyrazole, triazole, triazine, quinoline, and isoquinoline. Preferably, $R^3$ comprises a heteroaromatic ring derived from pyridine or imidazole. A substituent for the heteroaromatic ring $R^3$ can be selected from, but is not limited to, the group consisting of substituted and unsubstituted alkyl, carboxy, amino, alkoxy, thio, cyano, amide, sulfonyl, hydroxy, halide, perfluoroalkyl, aryl, ether, and ester. Preferably, the substituent for $R^3$ is selected from the group consisting of alkyl, sulfonyl, carboxy, halide, perfluoroalkyl, aryl, ether, and alkyl substituted with hydroxy, sulfonyl, carboxy, halide, perfluoroalkyl, aryl, or ether. When $R^3$ is a substituted pyridine, the substituent is preferably located at the 4-position. When $R^3$ is a substituted imidazole, the substituent is preferably located at the 3-position.

Representative examples of $R^3$ include 4-(dimethylamino)pyridinium-1-yl, 3-methylimidazolium-1-yl, 4-(pyrrolidin-1-yl)pyridinium-1-yl, 4-isopropylpyridinium-1-yl, 4-[(2-hydroxyethyl)methylamino]pyridinium-1-yl, 4-(3-hydroxypropyl)pyridinium-1-yl, 4-methylpyridinium-1-yl, quinolinium-1-yl, 4-tert-butylpyridinium-1-yl, and 4-(2-sulfoethyl)pyridinium-1-yl, shown below.

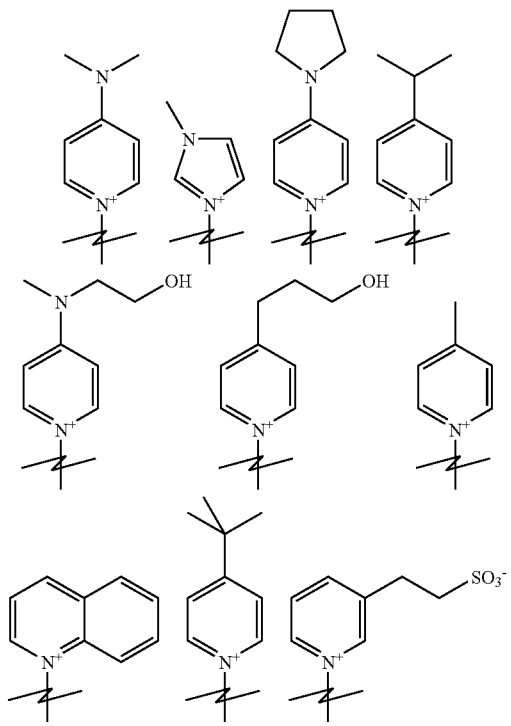

$R^3$ can also be represented by the following general structure:

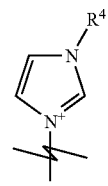

wherein $R^4$ is hydrogen or a substituted or unsubstituted alkyl group. More preferably, $R^4$ is selected from the group consisting of hydrogen, unsubstituted alkyl groups, and alkyl groups substituted with a hydroxy, ether, ester, sulfonate, or halide functional group. Most preferably $R^4$ is selected from the group consisting of propyl sulfonic acid, methyl, and oleyl.

$R^3$ can also be selected from heterocyclic rings such as, for example, morpholine, pyrrolidine, piperidine, and piperazine.

$M^+$ is preferably a noble metal cation. More preferably, $M^+$ is a Ag cation, a Au cation, or a Pt cation. Most preferably, $M^+$ is a Au cation. Another preferred metal cation is a Fe cation.

Preferred chromonic compounds can be represented by one of the following structures:

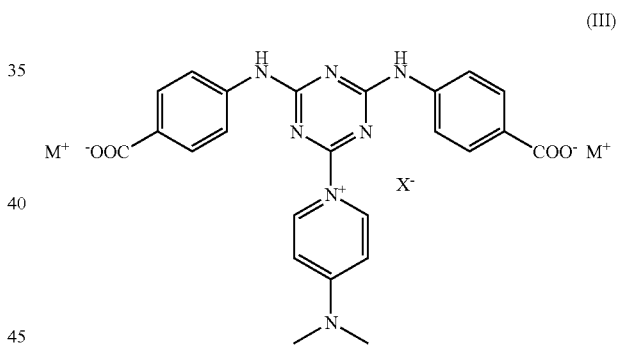

(III)

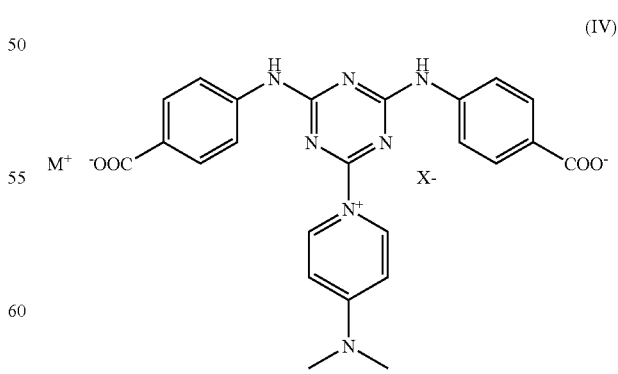

(IV)

wherein $X^-$ is a counterion. Preferably, $X^-$ is selected from the group consisting of $HSO_4^-$, $Cl^-$, $CH_3COO^-$, and $CF_3COO^-$.

Formula IV depicts the compound in its zwitterionic form. The pyridine nitrogen therefore carries a positive charge and one of the carboxy functional groups carries a negative charge (COO⁻).

The compounds of the invention can be prepared, for example, by starting with a chromonic starting compound represented by one of the following structures:

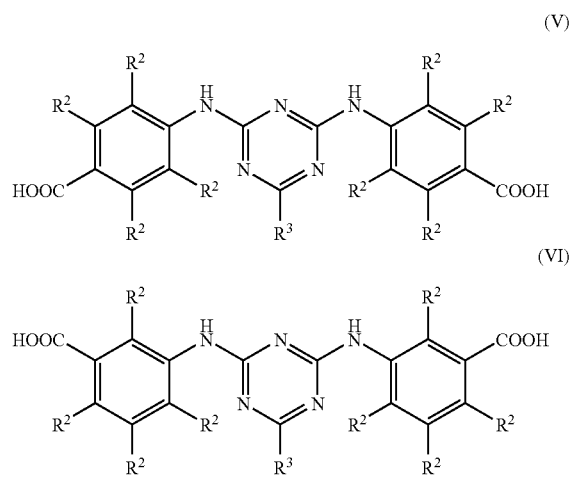

wherein $R^2$ is the same as described above.

As described in U.S. Pat. No. 5,948,487 (Sahouani et al.), which is herein incorporated by reference in its entirety, triazine derivatives such as the chromonic starting compound with formula V can be prepared as aqueous solutions. A typical synthetic route for the triazine molecules shown in formula V above involves a two-step process. Cyanuric chloride is treated with 4-aminobenzoic acid to give 4-{[4-(4-carboxyanilino)-6-chloro-1,3,5-triazin-2-yl]amino}benzoic acid. This intermediate is treated with a substituted or unsubstituted nitrogen-containing heterocycle. The nitrogen atom of the heterocycle displaces the chlorine atom on the triazine to form the corresponding chloride salt. The zwitterionic derivative can be prepared by dissolving the chloride salt in ammonium hydroxide and passing it down an anion exchange column to replace the chloride with hydroxide, followed by solvent removal. Alternative structures, such as that shown in formula VI above, may be obtained by using 3-aminobenzoic acid instead of 4-aminobenzoic acid.

These starting chromonic starting compounds can be placed in aqueous solution, for example, at room temperature. Generally, the chromonic starting compound will be added to the solution to achieve a concentration in the range of about 5 to about 20 (preferably, about 10) percent by weight of the solution. The starting chromonic compound in solution can then be mixed with an excess of noble or transition metal salt.

Preferred metal salts include noble metal salts. More preferred metal salts include silver salts (for example, silver nitrate, silver acetate, and the like), gold salts (for example, gold sodium thiomalate, gold chloride, and the like), platinum salts (for example, platinum nitrate, platinum chloride, and the like), and mixtures thereof. Most preferred metal salts include, silver nitrate, silver acetate, gold sodium thiomalate, gold chloride, and mixtures thereof. Iron salts are also preferred.

Precipitate can be rinsed away to remove excess metal, and then the solution can be dried (for example, by air and then in an oven at around 70° C.) to yield the chromonic compound of the invention.

Chromonic materials are capable of forming a chromonic phase or assembly when dissolved in an aqueous solution (preferably, an alkaline aqueous solution). Chromonic phases or assemblies are well known in the art (see, for example, Handbook of Liquid Crystals, Volume 2B, Chapter XVIII, Chromonics, John Lydon, pp. 981-1007, 1998) and consist of stacks of flat, multi-ring aromatic molecules. The molecules consist of a hydrophobic core surrounded by hydrophilic groups. The stacking can take on a number of morphologies, but is typically characterized by a tendency to form columns created by a stack of layers. Ordered stacks of molecules are formed that grow with increasing concentration.

It has been discovered that these tendencies make the chromonic compounds useful in methods for making metallic nanostructures. Metallic nanostructures can be made, for example, by depositing a solution comprising a chromonic compound of the invention to the surface of a substrate, and then reducing the metal.

Preferably, the chromonic compound of the invention is placed in aqueous solution in the presence of one or more pH-adjusting compounds and a surfactant. The addition of pH-adjusting compounds allows the chromonic material to become more soluble in aqueous solution. Suitable pH-adjusting compounds include any known base such as, for example, ammonium hydroxide or various amines. Surfactant can be added to the aqueous solution to promote wetting of the solution onto the surface of a substrate. Suitable surfactants include ionic and non-ionic surfactants (preferably, non-ionic). Optional additives such as viscosity modifiers (for example, polyethylene glycol) and/or binders (for example, low molecular weight hydrolyzed starches) can also be added.

Typically, the chromonic compound is dissolved in the aqueous solution at a temperature less than about 40° C. (more typically, at room temperature). One skilled in the art will recognize, however, that the geometry and size of the resulting metallic nanostructures can be controlled to some extent by varying the temperature.

The relative concentrations of each of the components in the aqueous solution will vary with the desired orientation of the resulting nanostructures and their intended application. Generally, however, the chromonic compound will be added to the solution to achieve a concentration in the range of about 4 to about 20 (preferably, about 4 to about 8) percent by weight of the solution.

The resulting solution can be applied to the surface of a substrate. Suitable substrates include any solid materials that will accept the application of the mixture (for example, glass or polymeric films).

The solution can be applied by any useful means that provides for the ordered arrangement of the chromonic materials such as, for example, by coating techniques such as wirewound coating rod or extrusion die methods. Preferably, shear orientation or magnetic orientation is applied either during or after application. The application of shear or magnetic force can help promote alignment of the chromonic compounds such that, upon drying, an oriented structure or matrix is obtained.

The metal can be reduced via reduction methods known in the art either before or after applying the mixture to the surface of a substrate. For example, the reduction can be accomplished by using a reducing agent (for example, tris(dimethylamino)borane, sodium borohydride, potassium borohydride, or ammonium borohydride), electron beam (e-beam) processing, or ultraviolet (UV) light.

After the metal is reduced, the coated layer can be dried. Drying of the coated layer can be achieved using any means suitable for drying aqueous coatings. Useful drying methods will not damage the coating or significantly disrupt the orientation of the coated layer imparted during coating or application.

After drying, the chromonic compound can be removed such that only metallic nanostructures remain on the substrate. The chromonic compound can be removed using any means such as, for example by heating to decomposition (for example, by heating to higher than about 300° C.). Alternatively, if the substrate is glass, the chromonic material can be removed with a basic solution.

The method described above can be used to make nanostructures such as, for example, nanowires and regular arrays of nanostructures (that is, arrays in which relatively uniformly sized and shaped nanostructures (for example, spherical nanoparticles) are substantially evenly spaced). The method of the invention can facilitate the fabrication of nanostructures over large areas, which can be advantageous, for example, for applications such as electro-magnetic interference (EMI) filters.

EXAMPLES

Objects and advantages of this invention are further illustrated by the following examples, but the particular materials and amounts thereof recited in these examples, as well as other conditions and details, should not be construed to unduly limit this invention.

Preparation of Silver Nanowires in a Chromonics Assembly

A mixture of purified water (9.0 g), ammonium hydroxide (0.25 g of a 30 weight percent aqueous solution, and the silver chromonic compound of Formula IV (1.0 g) was magnetically stirred for approximately 15 minutes. To this mixture there was added silver nitrate (0.6 g) and the mixture was magnetically stirred for an additional 15 minutes. The mixture was then filtered through filter paper and the isolated solid was washed with purified water. The isolated solid was dried in an oven at 60° C. for approximately 1 hour and was then dissolved in an approximately 10 weight percent aqueous solution of ammonium hydroxide. This mixture was coated onto a glass microscope slide using a #3 wound wire coating rod. The coating was allowed to dry for approximately 30 minutes in air at room temperature and then the coated glass slide immersed in a 3 weight percent solution of potassium borohydride in ethanol for approximately 1 minute. The coated glass slide was then rinsed with ethanol and was allowed to dry in air at room temperature for approximately 5 minutes. The dry coating was analyzed by optical microscopy using a Model DM4000M microscope (available from Leica Microsystems, Inc., Bannockburn, Ill.) at 1000 power. An optical micrograph of the coating is shown as a FIGURE. In the FIGURE, the thin light lines are the silver nanowires.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

I claim:

1. A compound selected from a group consisting of the following structures:

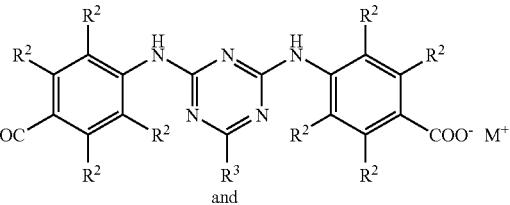

and

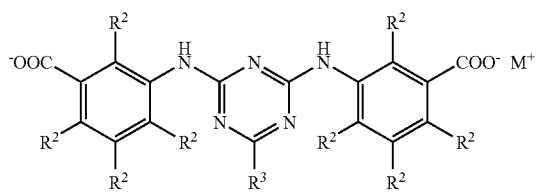

wherein
each $R^2$ is independently selected from the group consisting of hydrogen and substituted or unsubstituted alkyl groups,
$R^3$ is selected from the group consisting of substituted and unsubstituted heteroaromatic rings and substituted and unsubstituted heterocyclic rings, said rings being linked to the triazine group through a nitrogen atom within the of $R^3$, and when $R^3$, is a substituted or unsubstituted heteroaromatic ring and said substituted or unsubstituted heteroaromatic ring has a postive charge associated therewith, $R^3$ has a counterion $X^-$ associated therewith,
each $M^+$ is a noble metal cation; and
wherein the anionic and cation components of said structure are present at a molar ratio so as to result in an overall neutral charge.

2. The compound of claim 1 wherein each $R^2$ is independently selected from the group consisting of hydrogen, unsubstituted alkyl groups, alkyl groups substituted with a hydroxy or halide functional group, and alkyl groups having an ether, ester, or sulfonyl moiety therein.

3. The compound of claim 2 wherein $R^3$ is a substituted or unsubstituted heteroaromatic ring selected from the group consisting of substituted or unsubstituted pyridine, pyridazine, pyrimidine, pyrazine, imidazole, oxazole, isoxazole, thiazole, oxadiazole, thiadiazole, pyrazole, triazole, triazine, quinoline, and isoquinoline.

4. The compound of claim 3 wherein $R^3$ is a substituted or unsubstituted heteroaromatic ring selected from substituted or unsubstituted pyridine or imidazole.

5. The compound of claim 4 wherein $R^3$ is selected horn the group consisting of pyridinium-1-yl, 4-(dimethylamino) pyridinium-1-yl, 3-methylimidazolium-1-yl, 4-(pyrrolidin-1-yl)pyridinium-1-yl, 4-isopropyridinium-1-yl, 4[(2-hydroxyethyl)methylamino]pyridinium-1-yl, 4-(3-hydroxypropyl)pyridinium-1yl, 4methylpyridinium-1-yl, quinolinium-1-yl, 4-tert-butylpyridinium-1-yl, and 3-(2-sulfoethyl)pyridinium-1-yl.

6. The compound of claim 1 wherein each $M^+$ is selected from the group consisting of a Ag cation, a Au cation, and a Pt cation.

7. The compound of claim 6 wherein each $M^+$ is a Au cation.

8. The compound of claim 1 wherein each $M^+$ is a Fe cation.

9. The compound of claim 1 represented by following structure:

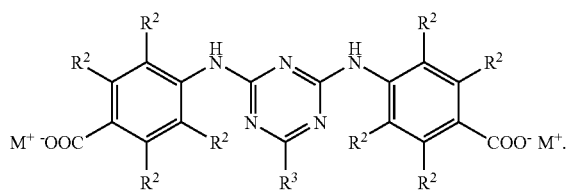

10. The compound of claim 9 represented by the following structure:

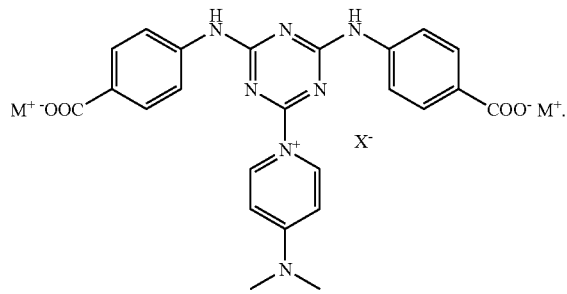

11. The compound of claim 10 wherein each M⁺ is a Au cation.

12. The compound of claim 10 wherein X⁻ is selected from the group consisting of $HSO_4^-$, $Cl^-$, $CH_3COO^-$, and $CF_3COO^-$.

13. A method of making oriented metallic nanostructures comprising (a) applying a solution comprising the compound of claim 1 to a surface of a substrate and (b) reducing the metal cation.

14. The method of claim 13 further comprising removing said at least one anionic component such that oriented metallic nanostructures remain or the surface.

15. A compound selected from a group consisting of the following structures:

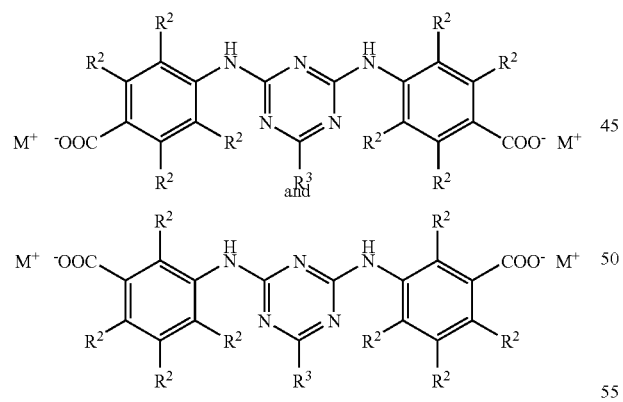

wherein
each $R^2$ is independently selected from the group consisting of hydrogen, unsubstituted alkyl groups, alkyl groups substituted with a hydroxy or halide functional group, and alkyl groups comprising an ether, ester, or sulfonyl moiety;
$R^3$ is a substituted or unsubstituted heteroaromatic ring selected from the group consisting of substituted or unsubstituted pyridine, pyridazine, pyrimidine, pyrazine, imidazole, oxazole, isoxazole, thiazole, oxadiazole, thiadiazole, pyrazole, triazole, triazine, quinoline, and isoquinoline, and when said substituted, or unsubstituted heteroaromatic ring has a positive charge associated therewith, $R^3$ has a counterion $X^-$ associated therewith;
each M⁺ is a noble metal cation; and
wherein the anionic and cation components of said structure are present at a molar ratio so as to result in an overall neutral charge.

16. A method of making metallic nanostructures comprising (a) applying a solution comprising the compound of claim 15 to a surface of a substrate and (b) reducing the metal cation.

17. The method of claim 16 further comprising:
orienting the solution on the surface of the substrate; and
removing said at least one amonic component such that oriented metallic nanostructures remain of the surface.

18. A compound of the following structure:

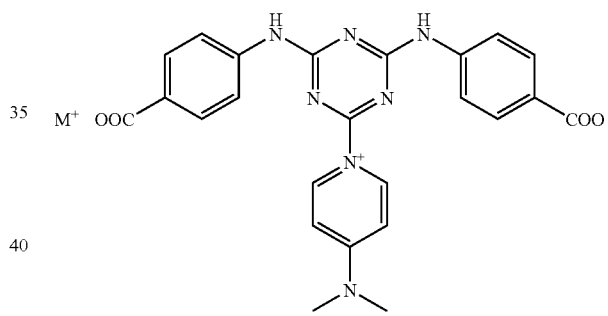

wherein
M⁺ is a metal cation selected from the group consisting of a Ag action, a Au cation and a Pt cation; and.
wherein the anionic and cation components of said structure are present at a molar ratio so as to result in an overall neutral charge.

19. A method of making metallic nanostructures comprising (a) applying a solution comprising the compound of claim 18 to a surface of a substrate and (b) reducing the metal cation.

* * * * *

UNITED STATES PATENT AND TRADEMARK OFFICE
CERTIFICATE OF CORRECTION

PATENT NO. : 7,247,723 B2
APPLICATION NO. : 10/996834
DATED : July 24, 2007
INVENTOR(S) : Hassan Sahouani It is certified that error appears in the above-identified patent and that said Letters Patent is hereby corrected as shown below:

On Title Page, Page 2,

Item (56)

Under "Other Publications", after "Metal" insert -- , --.

Column 8

Line 30, in Claim 1, after "within the" insert -- ring --.

Line 33, in Claim 1, delete "postive" and insert -- positive --, therefor.

Line 54, in Claim 5, delete "horn" and insert -- from --, therefor.

Column 9,

Line 38, in Claim 14, delete "or" and insert -- of --, therefor.

Column 10,

Line 12, in Claim 15, delete "substituted," and insert -- substituted --, therefor.

Line 26, in Claim 17, delete "amonic" and insert -- anionic --, therefor.

UNITED STATES PATENT AND TRADEMARK OFFICE
CERTIFICATE OF CORRECTION

PATENT NO. : 7,247,723 B2  Page 2 of 2
APPLICATION NO. : 10/996834
DATED : July 24, 2007
INVENTOR(S) : Hassan Sahouani It is certified that error appears in the above-identified patent and that said Letters Patent is hereby corrected as shown below:

Column 10 (Cont'd)

Lines 30-44, in Claim 18, delete

" 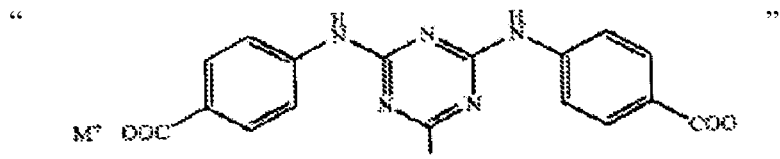 "

and insert

-- 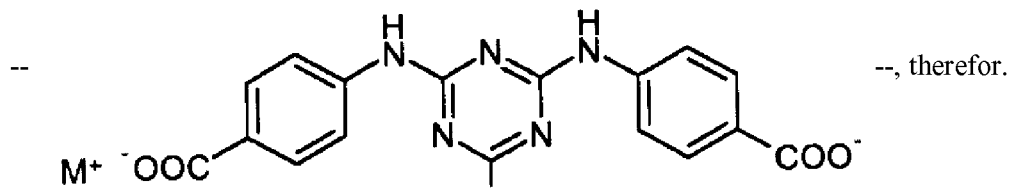 --, therefor.

Line 47, in Claim 18, delete "and." and insert -- and --, therefor.

Signed and Sealed this

Fifteenth Day of July, 2008

JON W. DUDAS
*Director of the United States Patent and Trademark Office*